United States Patent [19]

Hatzenbuhler et al.

[11] Patent Number: 5,275,946

[45] Date of Patent: Jan. 4, 1994

[54] THROMBOLYTIC AGENTS WITH MODIFIED KRINGLE DOMAINS

[75] Inventors: Nicole T. Hatzenbuhler; Keith R. Marotti; Edward F. Rehberg, all of Kalamazoo, Mich.; Johan H. Verheyen, Berkel en Rodenrÿs, Netherlands

[73] Assignee: Nederlandse Organisatie voor Toegepast-Natuurwetenschappelijk Onderzoek Tno, The Hague, Netherlands

[21] Appl. No.: 689,079

[22] PCT Filed: Oct. 4, 1989

[86] PCT No.: PCT/US89/04247

§ 371 Date: Jun. 7, 1991

§ 102(e) Date: Jun. 7, 1991

[30] Foreign Application Priority Data

Oct. 27, 1988 [U.S.] United States .................. 263673

[51] Int. Cl.$^5$ .................. C12N 9/48; C12N 9/64; C12N 15/09; C12N 15/58
[52] U.S. Cl. .................. 435/226; 424/94.64; 435/212; 435/219; 435/172.3
[58] Field of Search .................. 435/69.1, 212, 215, 435/226, 172.3, 320.1, 219; 424/94.63, 94.64; 536/23.2

[56] References Cited

FOREIGN PATENT DOCUMENTS 0234051 9/1987 European Pat. Off. .
0241208 10/1987 European Pat. Off. .
0273774 7/1988 European Pat. Off. .
0277313 10/1988 European Pat. Off. .
WO87/39906 7/1987 World Int. Prop. O. .

OTHER PUBLICATIONS

Lijnen, H. R. et al. Chem. Abstracts, vol. 10, No. 13 (Mar. 27, 1989).
van Zonneveld et al., "Autonomous functions of structural domains on human t-PA," *PNAS* 83:4670-4674 (1986).
Verheijen, J. H. et al., "Involvement of finger domain & kvingle z domain of t-PA in fibrin binding," *EMBO J.* 5(13):3525-3530 (1986).
Pannekoek, H. et al. "Mutants of human tPA:Structural aspects and functional properties" *Fibrinolysis* 2:123-132 (1988).

*Primary Examiner*—Robert A. Wax
*Assistant Examiner*—Dian C. Jacobson

[57] ABSTRACT

This invention relates to analogs of thrombolytic agents having a modified kringle domain. More specifically, this invention is directed to TPA type compounds wherein modifications occur in the kringle 1 and kringle 2 domains. This invention is also directed to analogs with one or more changes in the kringle domain of urokinase-type compounds. The compounds of this invention are pharmaceutically useful having particular use in the same manner as TPA and urokinase.

6 Claims, No Drawings

THROMBOLYTIC AGENTS WITH MODIFIED KRINGLE DOMAINS

FIELD OF INVENTION

This invention is to analogs of thrombolytic agents having a modified kringle domain. More specifically this invention is directed to TPA type compounds wherein modifications in the kringle 1 and kringle 2 domains occur. This invention is also directed to analogs with one or more changes in the kringle domain of urokinase-type compounds. The compounds of this invention are pharmaceutically useful having particular use in the same manner as TPA and urokinase.

BACKGROUND OF INVENTION

Plasminogen activators (PA's) are known to play a central role in the fibrinolytic process. Their mechanism of action involves conversion of the inactive proenzyme plasminogen to plasmin, an active serine protease, which in turn degrades the fibrin network of a clot. There are two known types of physiologically relevant PA's: urokinase-type plasminogen activators (uPA) and tissue-type plasminogen activators (TPA). TPA's are found to be far more specific in their action than uPA's showing a higher affinity for fibrin than uPA's and a specificity for the blood clot itself.

Tissue plasminogen activator (TPA) is a glycosylated 66,000 daltons serum protease of 527 amino acid residues produced by the vascular endothelial cells. It is a single polypeptide chain made up of five major domains: the fibronectin finger domain ($F_t$), the growth factor domain ($G_t$), the kringle 1 ($K_t1$) and kringle 2 ($K_t2$) domains and the active site ($A_t$). It is also known that TPA becomes activated upon binding to fibrin. When digested with plasmin, the one-chain TPA is cleaved at a single site (Arg 275-Ile 276) converting it to a two-chain form, a light and a heavy chain connected by a disulfide bridge. The light chain derived from the carboxy terminus contains the catalytic site. It has a great deal of homology with other serine proteases and does not bind fibrin. The heavy chain derived from the amino terminus is a multi-domain entity with homology to several other serine proteins. It contains a finger domain, a growth factor domain and two kringles. The kringles are triple disulfide structures. The heavy chain has been found to bind fibrin. TPA is cleared by the liver through the heavy chain.

Our recent results have shown that fibrin binding of TPA is localized in two domains. The finger domain contains a high affinity fibrin binding site and the kringle 2 domain a low affinity fibrin binding site. The affinity of the latter site is increased by plasminogen. Stimulation by fibrin and fibrinogen fragments however is mainly localized in the kringle 2 domain. Results obtained by another group (van Zonneveld and Pannekoek, CLB, Amsterdam) suggest stimulation by fibrin does not occur when K1 is directly coupled to the light chain. These results lead to the conclusion that the position of kringle 2 (adjacent to the light chain) and its structure are essential for its role in fibrin stimulation of activity. When we compare the amino acid sequences of TPA K2 with TPA K1, the uPA kringle, and the five plasminogen kringles there are only a limited number of amino acids that are unique for TPA K2. Particularly a group of amino acids around number 250 in the inner loop of the kringle is interesting in this respect.

Urokinase was first isolated from urine. It was then isolated from cultured cells, e.g., kidney cell lines and recently by expression of cDNA in *E. coli* or mammalian cells in culture. When urokinase is expressed in *E. coli*, it must be renatured.

Urokinase is a single polypeptide of 411 amino acid residues with a molecular weight of 55,000 daltons. This single chain form, also designated pro-urokinase (pro-u-PA) or single chain urokinase (scu-PA) has low activity, but it can be converted to a two-chain (tuc-PA) form by e.g., plasmin. The two chains stay connected to each other by a single disulfide bridge. In u-PA, three domains can be discerned - a growth factor ($G_u$), a kringle domain (Ku) and a protease domain ($P_u$).

The $G_u$ domain can interact with a cellular receptor. The $P_u$ domain contains the active site residues serine, histidine, and asparagine which are usually found in serine proteases. The function of the $k_u$ domain is unknown.

Homologous kringle domains also occur in plasminogen, factor XII, prothrombin and lipoprotein. In both t-PA and plasminogen, one or more kringle domains are involved in fibrin binding. This has not been observed in u-PA. Like t-PA, u-PA catalyses the conversion of the inactive proenzyme plasminogen to the active protease plasminogen. In the case of t-PA this conversion is greatly enhanced by fibrin, whereas for u-PA this is not the case. Nevertheless, fibrin specificity for u-PA has been observed. This observation has been explained by assuming that u-PA preferentially activates fibrin-bound plasminogen.

Since the fibrin specificity of t-PA and u-PA is based on a different mechanism, it should be possible in principle to combine the desired properties of both molecules in a single hybrid molecule. Such hybrids have been constructed, containing long pieces of u-PA and the fibrin binding domains of t-PA or plasminogen. The results are disappointing. Although some fibrin affinity is present in some hybirds, they do not compare to that of t-PA itself.

What is needed are novel t-PA and u-PA analogs which have a greater affinity for fibrin clots and a longer half-life.

INFORMATION DISCLOSURE

Patent application PCT WO 87/03906 published Jul. 2, 1987 describes TPA analogs comprising an active site, i.e., the protease domain, and one or more domains selected from the finger domain, the growth factor domain, the kringle 1 domain, and the kringle 2 domain wherein the domain regions have been altered from their native arrangement with respect to their order, occurrence, or both, provided that the overall molecular weight of the protein does not exceed 90,000 daltons and no domain appears more than twice. The compounds of the present invention are different from the compounds described in WO 87/03906 in that the kringle$_t$ 1 and kringle$_t$ 2 domains are modified and have a different amino acid sequence from that found in TPA. In addition, PCT WO 87/03906 does not teach urokinase analogs.

SUMMARY OF THE INVENTION

The present invention provides thrombolytic agents with one or more modified kringle domains.

The present invention further provides oligonucleotides having the following nucleotide sequence:
P106: SEQ I.D. No: 1

P107: SEQ I.D. No: 2
P108: SEQ I.D. No: 3
P109: SEQ I.D. No: 4
P110: SEQ I.D. No: 5
P111: SEQ I.D. No: 6
P112: SEQ I.D. No: 7
P114: SEQ I.D. No: 8
P115: SEQ I.D. No: 9
P116: SEQ I.D. No: 10
P117: SEQ I.D. No: 11
P118: SEQ I.D. No: 12
P120: SEQ I.D. No: 13
P121: SEQ I.D. No: 14
P122: SEQ I.D. No: 15
P123: SEQ I.D. No: 16

The present invention further provides TPA analog compounds wherein the kringle$_t$ domains are modified as follows: in kringle$_t$ 1 the amino acids at positions 160 to 165 are replaced by the amino acids found at positions 248 to 253 of kringle$_t$ 2; in kringle$_t$ 2 the amino acids at positions 248 to 253 are replaced by the amino acids found at positions 160 to 165 of kringle$_t$ 1. More specifically kringle$_t$ 1 is modified by substituting asparagine (N), arginine (R), arginine (R), leucine (L), threonine (T), tryptophan (W) respectively at positions 160 to 165. More specifically kringle$_t$ 2 is modified by substituting alanine (A), glycine (G), lysine (K), tyrosine (Y), serine (S), serine (S) respectively at positions 248 to 253. Thus the amino acids which normally occur at positions 160 to 165 in kringle$_t$ 1, i.e., A, G, K, Y, S, S are replaced by N, R, R, L, T, W, and the amino acids which normally occur at positions 248 to 253 of kringle$_t$ 2, i.e., N, R, R, L, T, W are replaced by A, G, K, Y, S, S. Hereinafter kringle$_t$ 1 and kringle$_t$ 2 modified as described above will be referred to as k$_t$1 and k$_t$2 respectively to distinguish these modified kringle$_t$ domains from the naturally occurring domains K$_t$1 and K$_t$2.

Another embodiment of the present invention relates to TPA analog compounds comprising an active or protease site (A) and one or more domains selected from the finger domain (F), the growth factor domain (G$_t$), the modified kringle 1 domain (k$_t$1), and the modified kringle 2 domain (k$_t$2) wherein the domain regions have been altered from the native arrangement with respect to their order, occurrence or both provided that no domain appears more than twice. Native arrangement means the relationship of the domains identified for native or naturally occurring TPA which is known to be FGK1K2A.

The present invention also provides a human u-PA analog that is a better thrombolytic agent than native u-PA in that it exhibits increased fibrin binding and/or better stimulation by fibrin or combination of other properties. The present invention focuses on the kringle region of u-PA wherein the kringle$_u$ is modified by replacing the amino acid residues at position 118-123 inclusive of u-PA with the amino acids found at position 248-253 inclusive of K$_t$2 of t-PA. More specifically, K$_u$ is modified by replacing glycine (G), Leucine (L), Lysine (K), Proline (P), Leucine (L) and Valine (V) with Asparagine (N), Arginine (R), Arginine (R), Leucine (L), Threonine (T) and Thyrptophan (W), respectfully.

The present invention describes the development of a human TPA analog that is a better thrombolytic agent than native TPA in that it exhibits one or more of the following properties: (1) a longer half-life than native TPA; (2) enhanced affinity for fibrin clots; and (3) lower or no binding to endogenous inhibitors, such as plasminogen activator inhibitor #1.

The present invention focuses on both of t-PA's kringle structures which have relatively conserved amino acid sequences. Only K$_t$2 appears to be vital to TPA's effectiveness for fibrin enhanced activity. The longest stretched of non-conserved sequence between kringle$_t$ 1 and kringle$_t$ 2 is six amino acids. It is thought that this stretch might be responsible for fibrin binding affinity of K$_t$2 versus K$_t$1. Therefore, this region is switched from kringle$_t$ 1 to kringle$_t$ 2 and vice versa. To accomplish this, both kringle$_t$ structures must be reassembled from oligonucleotides containing the desired changes.

The modified kringle$_t$ structures are enzymatically assembled from oligonucleotide fragments that are chemically synthesized using a solid-phase phosphoramidite triester coupling approach. After enzymatic assembly of the oligonucleotide fragments, each $kringle_t$ structure is individually cloned and successfully sequenced using the dideoxy sequencing methodology.

The key starting materials for making the compounds (to be used in making modified $kringles_t$) of the present invention are described in patent application PCT WO 87/03906 published Jul. 2, 1987, which is incorporated herein by reference.

In the present invention, small changes in the $K_u$ domain of u-PA are described which improve the fibrin binding properties, but do not alter the structure of the molecule very much. A u-PA molecule like this is possibly better for thrombolytic therapy than either naturally occurring t-PA or u-PA and may lead to a lower dosage (and cheaper treatment) with less side effects.

DETAILED DESCRIPTION OF INVENTION

As used herein, the domains of t-PA are denoted by subscript t. The domains of u-PA are denoted by subscript u.

As indicated hereinabove key starting materials for the preparation of the compounds of the present invention are described in patent application PCT WO 87/03906. These key starting materials are two prototype genes having unique endonuclease restriction sites between the domains of TPA designated herein $F_t$, $G_t$, $K_t1$, $K_t2$, and $A_t$ for the finger, growth factor, kringle 1, kringle 2, and protease or active site domains respectively. It should be noted that the kringle 1 ($K_t1$) and kringle 2 ($K_t2$) domains in the two prototype genes have the nucleotide sequence which would give the natural amino acid sequence as found in TPA. These two prototype genes are deposited in accordance with the Budapest Treaty. The host microorganisms are *E. coli* strains containing plasmids designated pTPA-B1,2,3,4(a) and pTPA-B1,2,3,4 and illustrated in Charts 1 and 2 respectively. The deposits were made with the Northern Regional Research Center, Peoria, Ill., USA. pTPA-B1,2,3,4(a) was deposited on Aug. 29, 1986 and assigned Accession Number NRRL B-18106. pTPA-B1,2,3,4 was deposited on Nov. 28, 1986 and assigned Accession Number NRRL B-18142.

Starting materials for the preparation of the compounds of the present invention are the DNA moieties for the modified $kringle_t$ structures which are enzymatically assembled from oligonucleotide fragments that were chemically synthesized using a solid-phase phosphoramidite triester coupling approach. After enzymatic assembly of the oligonucleotide fragments, each $kringle_t$ structure was individually cloned and sequenced using the dideoxy sequencing methodology.

The DNA sequence of the modified kringle 1 ($k_t1$) domain (block 3') is depicted in Chart 3 wherein the differences between the DNA sequences of the modified kringle$_t$ 1 and the natural kringle$_t$ 1 are noted with underlining. The DNA sequence of the modified kringle 2 domain ($k_t2$) (block 4') is depicted in Chart 4. In addition to modifying the DNA coding for the amino acids at positions 248 to 253 in kringle$_t$ 2 long stretches of guanosines (G) and cytidines (C) were eliminated. Each nucleotide change is marked with an asterisk (*). The dashed underlining portion of the sequence represents a linker at the 3'-end of the sequence for cloning purposes.

The materials and enzymes used in preparing the modified kringlet domains are obtained as follows. All the reagents for oligonucleotide synthesis are ordered from Applied BioSystems (ABI) except for acetonitrile and methanol (HPLC grade) which are both from Burdick and Jackson. Acetonitrile is dried by refluxing over calcium hydride followed by distillation. Acrylamide, bis-acrylamide, bromophenol blue, xylene cyanol and TEMED (tetramethylenediamine) are all purchased from BioRad. Urea is from Bethesda Research Laboratories. Lysozyme, flucose and ampicillin are obtained from Sigma. T4 polynucleotide kinase and T4 DNA ligase, as well as all the restriction enzymes are purchased from New England BioLabs. RNase A is from Pharmacia and Reverse Transcriptase from Seikagaku America, Inc. The dNTP's and ddNTP's are purchased from Pharmacia. $\gamma$-$^{32}p$ ATP and $\alpha$-$^{32}p$ dATP are ordered from Amersham. The E. coli AG1 competent cells come from Stratagene. The tryptone and yeast extract for Lennox Broth both are purchased from Difco Labs as in the antibiotic medium 2 for the agar plates. The nitrocellulose filters comes from Schleicher and Schuell.

All new oligonucleotides (P106, P107, P108-P112, P114-P118, P120-P123) required for the assembly of the modified kringle 1 ($k_t1$) and kringle 2 ($k_t2$) are synthesized on an ABI 380B DNA synthesizer using the solid-phase phosphoramidite triester coupling approach (S. L. Beaucage, M. H. Caruthers, Tetrahedron Letters 22:1859-1862, 1981). The oligonucleotides are cleaved off the support and partially deprotected using the synthesizer's deprotection program followed by treatment with concentrated ammonium hydroxide at 50° C. overnight. They are purified by polyacrylamide gel electrophoresis under denaturing conditions as previously described in detail (New York Theriault, et al., Nucleosides and Nucleotides 5:15-32, 1986). The oligonucleotides are sized by labeling with $\gamma$-$^{32}p$ ATP in the presence of T4 polynucleotide kinase and running a polyacrylamide gel under denaturing conditions against known standards.

The $k_t1$ DNA (block 3') is made using the same oligonucleotides as used for kringle$_t$ 1 DNA described in PCT WO 87/03906 except oligonucleotides P32 and P42 are replaced by P106 and P107 respectively in order to change the six amino acids as described above. The modified $k_t1$ block 3' is made up of a total of 20 oligonucleotides varying in length from a 21-mer to a 33-mer and has the structures set forth in Chart 4. The $k_t2$ DNA (block 4') is made using a total of 12 oligonucleotides varying in length from a 41-mer to a 50-mer. The structures of the oligonucleotides are depicted in Chart 4. Oligonucleotides P24 to P31, P33 to P41 and P43 are purchased from New England BioLabs. All the other oligonucleotides P106, P107, P108-P112, P114-P118, P120-P123 ranging in length from a 30-mer to a 50-mer are synthesized in very good yield (99.0%+per coupling).

The oligonucleotides are deprotected and purified by polyacrylamide gel electrophoresis using the conditions published by New York Theriault, et al., ibid. They are desalted on Waters SepPak C-18 cartridges. Their sizes and purities are confirmed by labeling with $\gamma$-$^{32}p$ ATP and polynucleotide kinase and running them on a polyacrylamide gel against known standards.

The $k_t1$ (block 3') is assembled following the strategy elaborated in Chart 5. The fragments are divided in two groups and ligated to yield I121 J125 and K148 L146. After purification and isolation, these are annealed and ligated to yield block 3'. After purification by polyacrylamide gel electrophoresis (10%) under non-denaturing conditions and isolation, block 3' is successfully cloned into pBR322, and sequenced by dideoxy methodology (E. Y. Chen, P. H. Seeburg, DNA 4:165-170, 1985; A. M. Maxam, W. Gilbert, Methods in Enzymol., 65:499-560, 1980).

The enzymatic assembly of $k_t2$ (block 4') is carried out as illustrated in Chart 6 and yielded M-182 N-185 and O-133 P-130. After purification and isolation these are annealed and ligated to yield block 4'. After purification by polyacrylamide gel electrophoresis (10%) under non-denaturing conditions and isolation, block 4' is cloned into pBR322 and sequenced as described above.

In cloning the modified kringle$_t$ 1 and modified kringle$_t$ 2 DNA the plasmids pBR322/Bam H1 and Cla 1, and pBR322/Bam H1 and Hind III are prepared. The circular pBR322 is cut with the appropriate restriction enzymes following the conditions outlined by the supplier for the enzymes being used. Purification is then done on a horizontal preparative 1% agarose gel in 1×E buffer (0.04M Tris acetate, 0.002M EDA) at 30 V overnight. The DNA was electroeluted from the agarose band in 0.5×E buffer at 50 V for 4 hours, phenol extracted, and ethanol precipitated.

After enzymatic assembly of the oligonucleotides to generate the desired sequence, each of the kringle$_t$ structures is ligated into its respective linear plasmid using T4 DNA ligase, 100 ng of plasmid DNA, and approximately 100-fold molar excess of insert DNA. The ligation is done in 20 $\mu$l of ligation buffer (0.5M Tris-HCl, pH 7.4; 0.1M MgCL$_2$; 0.1M DTT; 10 mM ATP) at 15° C. overnight. Equimolar amounts (0.2 nmol) of the gene fragments are labeled, annealed, ligated and the resulting ligated products purified as described previously in detail (New York Theriault, et al., ibid., and Biotechniques 6:470-474 (1988); Jay, et al., J. Biol. Chem. 259:6311-6317, TM (1984).

E. coli AG1 competent cells from Strategene are used for transformation of the plasmid/insert ligation reaction mixture. Transformations are done of each ligation reaction mixture, using 5 ng of reaction mixture DNA for each transformation. The transformations are done on ice for 30 minutes, heat shocked at 42° C. for 45 seconds, and then grown in L-broth at 37° C. for an hour before plating on agar plates containing ampicillin. Details of the procedure can be found in Maniatis, et al., Molecular Cloning, A Laboratory Manual, Cold Spring Harbor Laboratory, 1982, and in Stratagene's product information.

All positive transformants are identified by hybridization experiments with oligos used in the construction of the kringle$_t$ structures. The oligos chosen for hybrization are less than 25 bases long and have a base composition of approximately 50% G/C. The hybridizations and filter washes are done at different temperatures depending on the length of the oligonucleotides being used. Modified kringle$_t$1 is done 12 hours at 42° C. and washed with 0.1×SSC at 50° C. for 30 minutes and at 55° C. for 30 minutes with fresh SSC. The oligo being used is P25 which is a 24 mer and has 63% G/C content. Modified kringle$_t$ 2 is done at 42° C. for 72 hours with P48, a 23 mer with 43% G/C content. Washings are done the same way as for modified kringle$_t$ 1. It is finally washed with 0.2×SSC once at 42° C. Details of these protocols can be found in Maniatis, et al., ibid. Positive transformants are identified by autoradiography.

To make sure that the identified positive transformants contained the correct sequence without any mutations, at least one clone each of the modified kringle 1 (k$_t$1) and modified kringle 2 (k$_t$2) is completely sequenced by the dideoxy sequencing procedure (R. B. Wallace, et al., Gene 16:21-26, 1981; E. Y. Chen, P. H. Seeburg, ibid.) The positives from autoradiography are grown up overnight at 37° C. in 5 ml of L-broth containing ampicillin. Plasmid DNA is isolated from these overnight cultures by the alkaline lysis procedure. Details can be found in Maniatis, et al., ibid. From each of these overnight cultures enough DNA (about 250 ng) is isolated to run three sets of sequencing reactions. The DNA from the mini-preps is treated with DNase-free pancreatic RNase A (using 10 μg in 40 μl total volume) for one hour at 37° C. The RNase is removed by phenol extraction and the DNA was ethanol precipitated. The DNA is denatured with 2N NaOH/2 mM EDTA for 10 to 20 minutes at room temperature. Priming with the sequencing templates is done during ethanol precipitation. Dideoxy sequencing is done with reverse transcriptase following standard procedures for sequencing of double-stranded DNA. Primers for sequencing are ones that are available from New England BioLabs and/or oligonucleotides that were used in the assembly of blocks 3' and 4'.

The kringles of t-PA (K$_t$1, K$_t$2) are very similar to that of u-PA (K$_u$). Therefore, analogous changes as made in t-PA K$_t$1 and giving it fibrin-binding properties are made in u-PA K. Specifically, the residues numbered 118 to 123 in u-PA, glycine, leucine, lysine, proline, leucine, valine (GLKPLV) are replaced by the residues in the analogous position of t-PA K2 numbered 248 to 253-asparagine, arginine, arginine, leucine, threonine, and tryptophan (NRRLTW). Such changes can be accomplished in different ways, but the alteration of a DNA coding for u-PA is the most convenient method. The altered protein can be produced by expression of this altered DNA in a bacterial or mammalian expression system. The DNA can be changed using oligonucleotide directed mutagenesis with DNA coding for u-PA as a staring material. cDNA coding for u-PA has been described. A fragment of u-PA cDNA coding for at least that part of the kringle$_u$ to be mutated is cut from the cDNA, using one or more restriction endonucleases and isolated with agarose gel electrophoresis and cloned in a commercially available cloning vector. The resulting plasmid is used for mutagenesis using published protocols or commercially available kits. Alternatively, a complete synthetic cDNA coding for the altered u-PA is constructed. Such construction requires oligonucleotides synthesized according to available protocols. An advantage of the latter method is that the DNA sequence can differ from the natural one and comprise one or more unique restriction enzyme recognition sequences greatly facilitating further alterations A. Preparation of t-PA analogs The specific examples set forth below teach the preparation of plasmids containing cDNA encoding illustrative TPA analogs containing modified kringle 1 (k$_t$1) or modified kringle 2 (k$_t$2). Conventions used to represent plasmids and fragments in Charts 1-7 are meant to by synonymous with conventional representations of plasmids and their fragments. Unlike the conventional circular figures, the single line figures on the charts represent both circular and linear double-stranded DNA. With respect to the orientation of the resin sequence only the initiation of transcription is depicted as occurring from left to right (5' to 3'). Asterisks (*) represent the bridging of nucleotides to complete the circular form of the plasmids. Fragments do not have asterisks because they are linear pieces of double-stranded DNA. Endonuclease restriction sites are indicated above the line. Gene markers are indicated below the line.

The various symbols used in Charts 1-7 have the following meanings in respect to t-PA:

F=finger domain
G=growth factor domain
K1=Kringle 1 domain
K2=Kringle 2 domain
N=noncoding 3' sequence
k1=Modified Kringle 1 domain
k2=Modified Kringle 2 domain
A=active site
L=TPA leader sequence
T=5' region of TPAcDNA
P=middle region of TPAcDNA
a=polyadenylation signal sequence
AmpR=ampicillin resistance
Ori=pBR322 origin of replication
SV40=simian virus origin of replication
dhfr=mouse dihydrofolate reductase marker
CMV=cytomegalovirus promoter

EXAMPLE 1

Construction of FGk1A plasmid

Digest plasmid pTPA-B1, 2, 3, 4 (see Chart 2) partially with Hpa I and Mst I and isolate the 4 kb fragment. This digest deletes the K2 region. The 4 kb fragment is then ligated together to generate the FGK1A plasmid. The FGK1A plasmid is digested with Cla I and Bam HI which yields a 3.8 kb fragment with the K1 region deleted. The deleted K1 region can now be replaced with the Cla/Bam HI k1 fragment by ligating it to the 3.8 kb fragment (with the K1 region deleted) thereby generating the analog FGk1A.

EXAMPLE 2

Construction of FGk2A plasmid

The plasmid pTPA-B1, 2, 3, 4 is digested with EcoRV and Xma III. The 4 kb fragment is isolated and ligated to the 230 bp k2 fragment obtained by digesting the plasmid containing block 4' (pBR322 Bam HI/Hind III) with Hpa I and Xma III. The resulting plasmid contains the FGk2A construct.

EXAMPLE 3

Construction of FGk1K2A plasmid

The plasmid pTPA-B1, 2, 3, 4 is digested with Cla I and Bam HI and the 4 kb fragment is isolated. The plasmid containing block 3' is digested with Cla I and Bam HI and the 270 bp fragment containing the $k_t1$ is isolated. The 4 kb ClaI/Bam HI is then ligated to the 270 bp ClaI/Bam HI fragment to yield the plasmid containing FGk1K2A.

EXAMPLE 4

Construction of pTPA-IE-FGk1A

The construction of pTPA0IE-FGk1A is a two step process. Step one involves the creation of pTPA-FGk1A which contains the desired TPA analog, the polyadenylation signal sequence from BGH and the selectable markers and replicons of pSVCOW and Step 2 involves the insertion of the CMV I.E. promoter. While the example below describes the insertion of TPA analog FGk1A, other analogs (e.g., FGk1K2A or FGk2A) can be inserted using the same enzymes and procedures (see Chart 7).

Plasmid pTPA-CDNA (described in Chart 21, page 77 of PCT/US86/02684) is cut with Bam HI and Bgl II to yield a 120 base pair fragment which is gel isolated. Plasmid pSVCOW7 (described in Chart 20, page 76 of PCT/US86/02684) is cut with Eco RI and Pvu II to yield a 600 base pair fragment containing the polyadenylation sequence of bovine growth hormone which is gel isolated. The TPA analog sequence is obtained by cutting plasmid pFGk1A (Example 1 above) with Bgl II and Bal I to obtain a 1.7 kilobase fragment which is gel isolated. A second sample of pSVCOW7 is cut with Eco RI and Bam HI to yield a 5.8 kilobase fragment containing the markers and replicons of pSVCOW7 which are gel isolated. The four isolated fragments are ligated using T4 ligase to yield plasmid pTPA-FGk1A (8.2 kb) which is then cut with Bam HI, and the CMV-IE promoter (760 bp) is inserted to form plasmid pTOA-IE-FGk1A. The CMV-IE promoter is obtained from a Pst I and Sau 3A digestion of the human CMV genome.

EXAMPLE 5

Transfection and Culturing of CHO cells

Plasmid pTPA-IE-FGk1A is transfected into Chinese hamster ovary (CHO) cells deficient in dihydrofolate reductase (dhfr) using the calcium phosphate method for transfection of DNA into cells which is described in detail by Graham, et al. (in Introduction of Macromolecules into Viable Mammalian Cells, Alan R. Liss, Inc., New York, 1980, pp. 3-25). The cell line used is the mutant DXB-11 originally available from L. Chasin of Columbia University and completely described in Proc. Natl. Acad. Sci. USA 77:4216-4220 (1980). The above method for transfection relies on the fact that cells which incorporate the transfected plasmids are no longer dhfr deficient and will grow in Dulbecco's modified Eagle's medium plus proline.

From the cells transfected with pTPA-IE-FGk1A, clones are isolated, which, when grown in a monolayer for two days, synthesize at least 10 ng FGk1A per million cells. From cells with pIETPA-FGk1A-dhfr clones are isolated which synthesize at least 100 ng TPA per million cells. Expression of the TPA analog can be detected by radioimmunoassay, enzymatic assay or Western blot techniques.

The following Table 1 demonstrates the production of the TPA analogs by CHO cells. The following Table 2 shows that by replacing the 6 amino acids in Kringle$_t$1 with the 6 amino acids from Kringle$_t$2, we have given $k_t1$ properties similar to $K_t2$, i.e., FGk1A activity is now stimulated in the presence of fibrin.

TABLE 1

| Analog | I.U./ml* |
|---|---|
| Control medium | 0.4 |
| FGk1A | 92.3 |
| FGk1K2A | 112.9 |

*Determined by using a chromogenic assay including plasminogen, the synthetic substrate S-2251, and CNBr-digested fibrinogen.

TABLE 2

| | $\Delta A405/min^2$-M ($\times 10^3$) | | |
|---|---|---|---|
| Analog | −Fibrinogen Fragments | +Fibrinogen Fragments | Enhancement Factor |
| FGK1A | 29.2 | 228 | 7.8 |
| FGk1A | 18.5 | 2,180 | 117.8 |

B. Preparation of u-PA analogs

The specific example set forth below teach the preparation of plasmids containing cDNA encoding illustrative u-PA analogs containing the modified kringle$_u$.

EXAMPLE 6

1. cDNA is prepared from polyA+RNA isolated from HT1080 and polymerase chain-reaction (PCR) technique with SEQ ID NO: 17 (oligonucleotide #1$_u$) and SEQ ID NO: 18 (oligonucleotide #2$_u$). These primer. From this cDNA, u-PA coding cDNA is amplified with the polymerase chain-reaction (PCR) technique with 5'-AGCAGATCGGAGACCGCAG-3'(oligonucleotide #1$_u$) and 5'-TGGCCAGAGGGGTCTGGGCA-3' (oligonucleotide #2$_u$). These oligonucleotides are derived from the published sequence of u-PA cDNA.

2. Commercially available linkers containing a HindIII recognition sequence are ligated to the amplified cDNA for u-PA. The resulting fragment is cut with HindIII and inserted in HindIII digested pUC plasmid. The resulting plasmid pUC u-PA is used for site directed mutagensis.

3. An expression plasmid is constructed from pUC u-PA (PUC is available from Pharmacia) and a peV2 t-PA, a t-PA expression plasmid previously described by J. H. Verheijen et al, EMBO Journal, Vol, 5, pp. 3525-3530 (1986). The plasmid pUC u-PA is cut with HindIII and StuI and the small fragment containing the u-PA coding sequence is isolated. Plasmid peV2 pre-t-PA, a derivative of peV2 t-PA (Verheijen et al), containing a SV40 promoter followed by the t-PA signal sequence and the rabbit β-globin poly-A signal, but missing most of the t-PA coding sequence, is cut with BglIII, made blunt ended with nuclease, and cut with HindIII. The large fragment is isolated and ligated with the HindIII-StuI fragment from pUC u-PA. The resulting plasmid p2V2 u-PA contains the SV40 promoter followed by the u-PA coding sequence and the rabbit β-globin poly-A signal.

4. Mutagensis is performed in the pUC u-PA using the protocol of Marotti, K. et al. Gene Analysis Techniques, 6:67-70 1989. One of the following nucleotides, SEQ ID NO: 19 (oligonucleotide #3$_u$) or SEQ ID NO: 20 (oligonucleotide #4$_u$) is used for mutagenesis.

4. Alternatively, the procedure can be performed in two steps using the protocol of Marotti et al. First, the nucleotides coding for the six amino acids (GLKPLV) originally present in u-PA are removed using oligonucleotides SEQ ID NO: 21 (oligonucleotide #5$_u$) or oligonucleotide SEQ ID NO: 22 (oligonucleotide #6ᵤ) followed by the insertion of (NRRLTW) using oligonucleotides 3ᵤ or 4ᵤ.

5. The presence of the mutation and the absence of any secondary mutations is confirmed by sequencing using a Boehringer Mannheim kit.

6. The plasmid is transfected into CHO cells and the cloned expressed urokinase analog is isolated according to the method of J. H. Verheijen et al, EMBO Journal, Vol. 5, pp. 3525-3530 (1986).

CHART 1
Plasmid pTPA-B1, 2, 3, 4a

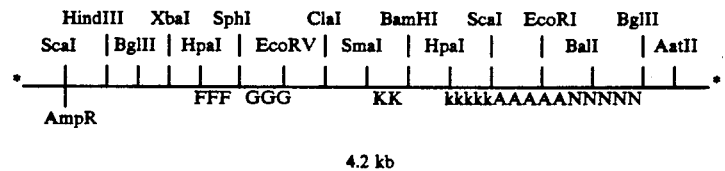

CHART 2

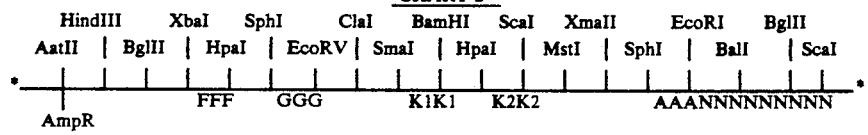

pTPA-B1, 2, 3, 4

CHART 3

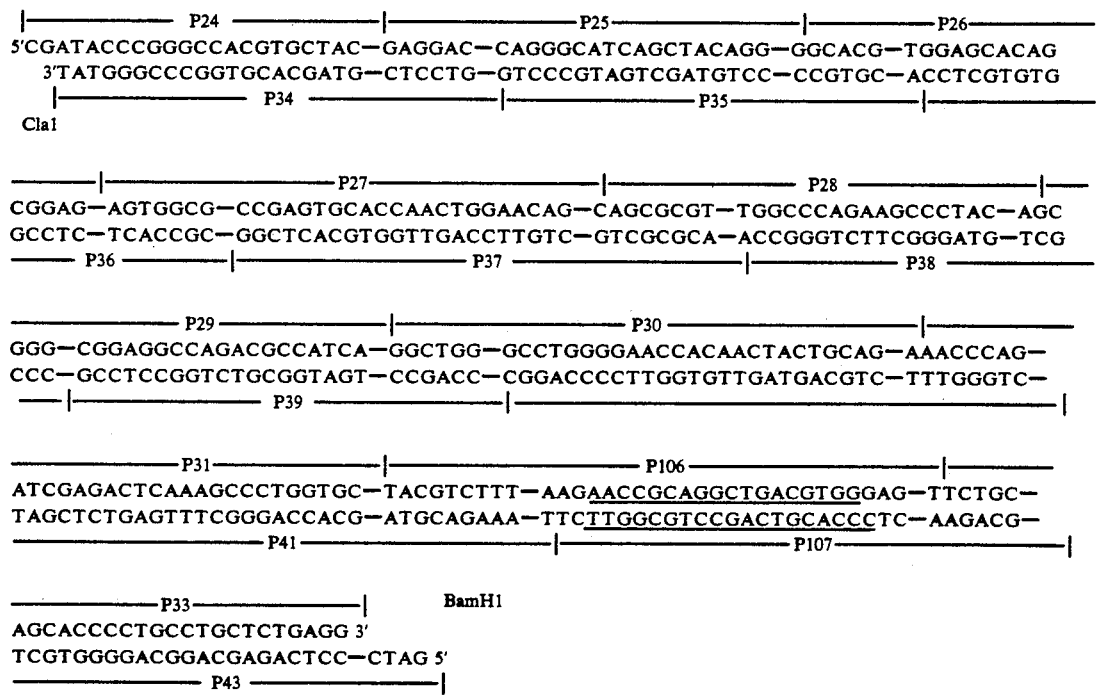

CHART 4

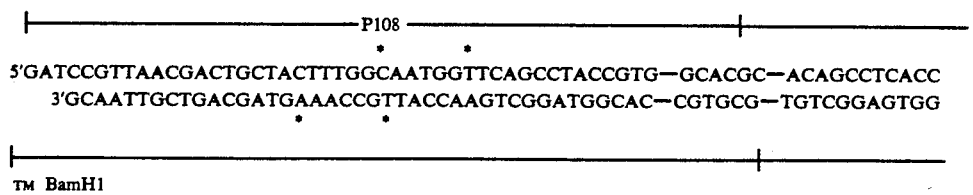

-continued
CHART 4

```
 ————————P109————————————|———————————P110——————————
         •          •           •                                •
GAGTCAGGTGCCTCATGCCTTCCGTGGAAT—TCCATG—ATCCTGATAGGCAAGGTTTACACAGCAC
CTCAGTCCACGGAGTACGGAAGGCACCTTA—AGGTAC—TAGGACTATCCGTTCCAAATGTGTCGTG
         •          •           •                                •
                               |—————————P116—————————————

——————————|———————————P111——————————|                          •
    • ••   •              •
AGAATCCTAGTGCTC—AGGCACT—GGGACTCGGCAAACATAATTACTGCCGGAATCCT—GATGGCG—
TCTTAGGATCACGAG—TCCGTGA—CCCTGAGCCGTTTGTATTAATGACGGCCTTAGGA—CTACCGC—
    • ••   •              •
 ———————————————————————————————|——————————————————————————————|

———————P112————————|————————————P120—————————
         •          •••••••••  ••••••• •                        •
ATGCCAAGCCATGGTGCCACGTGCTGAAGGCAGGTAAGT—ACAGCTC—AGAGTACTGTGATGTGCCT
TACGGTTCGGTACCACGGTGCACGACTTCCGTCCATTCA—TGTCGAG—TCTCATGACACTACACGGA
         •          •••••••••  ••••••• •                        •
 ———————P118———————|————————————P122—————————

——————————P121——————————
TCCTGCGCAACCGCA—TGC—GGC—CGGAGATACAGCCAGCCTCAGTTTCGCATCAAAGGA
AGGACGCGTTGGCGT—ACG—CCG—GCCTCTATGTCGGTCGGAGTCAAAGCGTAGTTTCCT
                      ——————————————————————|
                          ——————————P123——————————
```

```
———————| HindIII
GGTA 3'
CCATTCGA 5'

————————|
5'
```

CHART 5

```
 P24  P25  P26  P27  P28
                         —T4 DNA— I-121
                          ligase  J-125
 ——   ——   ——   ——   ——
 P34  P35  P36  P37  P38
ClaI
```

-continued
CHART 5

```
                                            —T4 DNA— M-269
                                             ligase  N-271
              P29  P30  P31  P106  P33  BamH1
 45
                                            —T4 DNA— K-148
                                             ligase  L-146
 50           P39  P40  P41  P107  P43
```

CHART 6

```
 P108  P109  P110  P111
                          —T4 DNA——— M-182
                           ligase    N-185
 P114  P115  P116  P117
BamH1                                         —T4 DNA——— A-315
                                               ligase    B-315
 P112  P120  P121
                          —T4 DNA——— O-133
                           ligase    P-130
 P118  P122  P123
HindIII
```

CHART 7

```
BamHI               BglII
 |——————————————————|
   L L L L L L L L L L
```

-continued

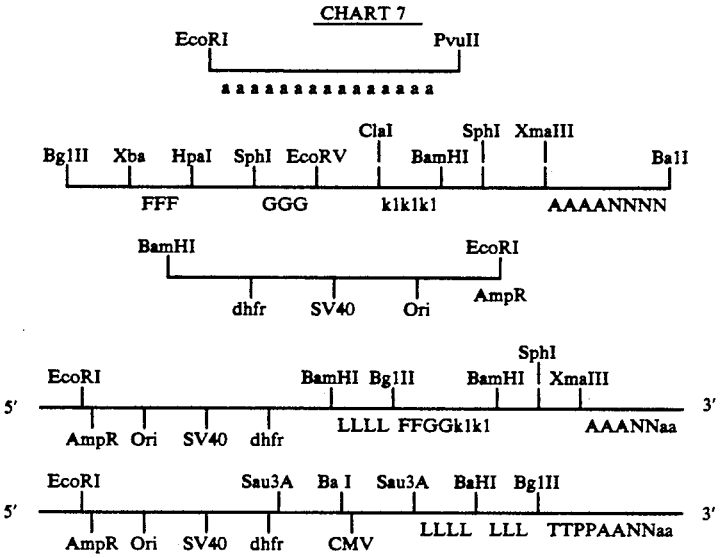

CHART 7

| SEQUENCE LISTING | |
|---|---|
| (1) GENERAL INFORMATION: | |
| (i) APPLICANT: | Nicole T. Hatzenbuhler; Keith R. Marotti; Edward F. Rehberg; and Johan H. Verheijen |
| (ii) TITLE OF INVENTION: | Thrombolytic Agents with Modified Kringle Domains |
| (iii) NUMBER OF SEQUENCES: | 22 |
| (iv) CORRESPONDENCE ADDRESS: | Dvorak and Traub |
| (A) ADDRESSEE: | Livia Boyadjian, Esq. |
| (B) STREET | 20 Exchange Place, 37th Floor |
| (C) CITY | New York |
| (D) STATE | New York |
| (E) COUNTRY | United States |
| (F) ZIP | 10005 |
| (v) COMPUTER READABLE FORM: | |
| (A) MEDIUM TYPE: | Floppy Disc |
| (B) COMPUTER | IBM-PC Compatible |
| (C) OPERATING SYSTEM | MS-DOS, IBM-DOS |
| (D) SOFTWARE: ~ | Wordperfect 5.1 |
| (vi) CURRENT APPLICATION DATA (if available): | |
| (A) APPLICATION NUMBER: | 07/689,079 |
| (B) FILING DATE | June 7, 1991 |
| (C) CLASSIFICATION | |
| (vii) PRIOR APPLICATION DATA (if applicable) | |
| (A) APPLICATION NUMBER: | PCT/US89/04247 |
| (B) FILING DATE | October 4, 1989 |
| (viii) ATTORNEY/AGENT INFORMATION: | |
| (A) NAME: LIVIA BOYADJIAN | |
| (B) REGISTRATION NUMBER: | (34,781) |
| (C) REFERENCE/DOCKET NUMBER: | 2212.LB-6818 |
| (ix) TELECOMMUNICATION INFORMATION: | |
| (A) TELEPHONE: | (212) 968-1300 |
| (B) TELEFAX: | (212) 968-1307 |
| (C) TELEX: | 232843 |
| (D) CABLE: | WORLDLEGIS NY |

(2)
SEQ ID NO: 1
LENGTH :33
TYPE :nucleotide
STRANDEDNESS :single
TOPOLOGY :linear
SEQUENCE DESCRIPTION :
TACGTCTTTA AGAACCGCAG GCTGACGTGG GAG      33
SEQ ID NO: 2
LENGTH :30
TYPE :nucleotide
STRANDEDNESS :single
TOPOLOGY :linear
SEQUENCE DESCRIPTION :
GCAGAACTCC CACGTCAGCC TGCGGTTCTT      30
SEQ ID NO: 3
LENGTH :45
TYPE :nucleotide
STRANDEDNESS :single

SEQUENCE LISTING

TOPOLOGY :linear
SEQUENCE DESCRIPTION :
GATCCGTTAA CGACTGCTAC TTTGGCAATG GTTCAGCCTA CCGTG    45
SEQ ID NO: 4
LENGTH :47
TYPE :nucleotide
STRANDEDNESS :single
TOPOLOGY :linear
SEQUENCE DESCRIPTION :
GCACGCACAG CCTCACCGAG TCAGGTGCCT CATGCCTTCC GTGGAAT    47
SEQ ID NO: 5
LENGTH :49
TYPE :nucleotide
STRANDEDNESS :single
TOPOLOGY :linear
SEQUENCE DESCRIPTION :
TCCATGATCC TGATAGGCAA GGTTTACACA GCACAGAATC CTAGTGCTC    49
SEQ ID NO: 6
LENGTH :41
TYPE :nucleotide
STRANDEDNESS :single
TOPOLOGY :linear
SEQUENCE DESCRIPTION :
AGGCACTGGG ACTCGGCAAA CATAATTACT GCCGGAATCC T    41
SEQ ID NO: 7
LENGTH :46
TYPE :nucleotide
STRANDEDNESS :single
TOPOLOGY :linear
SEQUENCE DESCRIPTION :
GATGGCGATG CCAAGCCATG GTGCCACGTG CTGAAGGCAG GTAAGT    46
SEQ ID NO: 8
LENGTH :47
TYPE :nucleotide
STRANDEDNESS :single
TOPOLOGY :linear
SEQUENCE DESCRIPTION :
GCGTGCCACG GTAGGCTGAA CCATTGCCAA AGTAGCAGTC GTTAACG    47
SEQ ID NO: 9
LENGTH :47
TYPE :nucleotide
STRANDEDNESS :single
TOPOLOGY :linear
SEQUENCE DESCRIPTION :
CATGGAATTC CACGGAAGGC ATGAGGCACC TGACTCGGTG AGGCTGT    47
SEQ ID NO: 10
LENGTH :50
TYPE :nucleotide
STRANDEDNESS :single
TOPOLOGY :linear
SEQUENCE DESCRIPTION :
AGTGCCTGAG CACTAGGATT CTGTGCTGTG TAAACCTTGC CTATCAGGAT    50
SEQ ID NO: 11
LENGTH :41
TYPE :nucleotide
STRANDEDNESS :single
TOPOLOGY :linear
SEQUENCE DESCRIPTION :
CGCCATCAGG ATTCCGGCAG TAATTATGTT TGCCGAGTCC C    41
SEQ ID NO: 12
LENGTH :46
TYPE :nucleotide
STRANDEDNESS :single
TOPOLOGY :linear
SEQUENCE DESCRIPTION :
GAGCTGTACT TACCTGCCTT CAGCACGTGG CACCATGGCT TGGCAT    46
SEQ ID NO: 13
LENGTH :41
TYPE :nucleotide
STRANDEDNESS :single
TOPOLOGY :linear
SEQUENCE DESCRIPTION :
ACAGCTCAGA GTACTGTGAT GTGCCTTCCT GCGCAACCGC A    41
SEQ ID NO: 14
LENGTH :46
TYPE :nucleotide
STRANDEDNESS :single
TOPOLOGY :linear
SEQUENCE DESCRIPTION :
TGCGGCCGGA GATACAGCCA GCCTCAGTTT CGCATCAAAG GAGGTA    46
SEQ ID NO: 15

-continued

SEQUENCE LISTING

LENGTH :40
TYPE :nucleotide
STRANDEDNESS :single
TOPOLOGY :linear
SEQUENCE DESCRIPTION :
GCCGCATGCG GTTGCGCAGG AAGGCACATC ACAGTACTCT   40
SEQ ID NO: 16
LENGTH :44
TYPE :nucleotide
STRANDEDNESS :single
TOPOLOGY :linear
SEQUENCE DESCRIPTION :
AGCTTACCTC CTTTGATGCG AAACTGAGGC TGGCTGTATC TCCG   44
SEQ ID NO: 17
LENGTH :19
TYPE :nucleotide
STRANDEDNESS :single
TOPOLOGY :linear
SEQUENCE DESCRIPTION :
AGCAGATCGG AGACCGCAG   19
SEQ ID NO: 18
LENGTH :20
TYPE :nucleotide
STRANDEDNESS :single
TOPOLOGY :linear
SEQUENCE DESCRIPTION :
TGGCCAGAGG GGTCTGGGCA   20
SEQ ID NO: 19
LENGTH :45
TYPE :nucleotide
STRANDEDNESS :single
TOPOLOGY :linear
SEQUENCE DESCRIPTION :
TGGTGCTATG TGCAGGTGAA CCGCAGCCTG ACGTGGCAAG AGTGC   45
SEQ ID NO: 20
LENGTH :45
TYPE :nucleotide
STRANDEDNESS :single
TOPOLOGY :linear
SEQUENCE DESCRIPTION :
GCACGCTTGC CACGTCAGGC TGCGGTTCAC CTGCACATAG CACCA   45
SEQ ID NO: 21
LENGTH :36
TYPE :nucleotide
STRANDEDNESS :single
TOPOLOGY :linear
SEQUENCE DESCRIPTION :
TGGTGCTATG TGCAGGTGCA AGAGTGCATG GTGCAT   36
SEQ ID NO: 22
LENGTH :36
TYPE :nucleotide
STRANDEDNESS :single
TOPOLOGY :linear
SEQUENCE DESCRIPTION :
ATGCACCATG CACTCTTGCA CCTGCACATA GCACCA   36

We claim:

1. A tissue plasminogen activator (tPA) compound comprising the tPA active site ($A_t$) and a modified tPA kringle 1 domain ($k_t1$) in which the amino acid sequence Ala Gly Lys Tyr Ser Ser at positions 160-165 is replaced by the amino acid sequence Asn Arg Arg Leu Thr Trp, and a combination of any or none of the tPA finger domain ($F_t$), the tPA growth factor domain ($G_t$), the natural tPA kringle domains ($K_t1$, $K_t2$), and a modified tPA kringle 2 domain ($k_t2$) in which the amino acid sequence Asn Arg Arg Leu Thr Trp at positions 248-253 is replaced by the amino acid sequence Ala Gly Lys Tyr Ser Ser.

2. The tissue plasminogen activator compound of claim 1, selected from the group consisting of $F_t k_t1 A_t$,
$F_t G_t k_t1 A_t$,
$k_t1 k_t2 A_t$,
$F_t k_t1 k_t2 A_t$,
$F_t G_t k_t1 K_t2 A_t$, and
$G_t k_t1 k_t2 A_t$.

3. The tissue plasminogen activator compound of claim 1, selected from the group consisting of $F_t G_t k_t1 k_t1 A_t$,
$F_t G_t k_t2 k_t1 A_t$,
$F_t F_t k_t1 k_t2 A_t$, and
$F_t F_t G_t k_t1 k_t2 A_t$.

4. The tissue plasminogen activator compound of claim 2, wherein the compound is $F_t G_t k_t1 K_t2 A_t$.

5. The tissue plasminogen activator compound of claim 1, selected from the group consisting of $G_t k_t1 K_t2 A_t$,
$F_t k_t1 K_t2 A_t$, and
$k_t1 K_t2 A_t$.

6. A compound of any of claims 1-3, whose molecular weight is no more than 90 kD.

* * * * *